US 6,731,216 B2

United States Patent
Ho et al.

(10) Patent No.: US 6,731,216 B2
(45) Date of Patent: May 4, 2004

(54) PROPER TUBING INSTALLATION TESTING METHOD AND APPARATUS FOR A PERISTALTIC PUMP

(75) Inventors: Chen Ho, Plano, TX (US); Thinh Vo, Garland, TX (US); Roger J. Hill, Richardson, TX (US)

(73) Assignee: B. Braun Medical, Inc., Carrollton, TX (US)

( * ) Notice: Subject to any disclaimer, the term of this patent is extended or adjusted under 35 U.S.C. 154(b) by 79 days.

(21) Appl. No.: 10/151,339

(22) Filed: May 20, 2002

(65) Prior Publication Data

US 2003/0214412 A1 Nov. 20, 2003

(51) Int. Cl.⁷ .............................................. G08B 21/00
(52) U.S. Cl. ....................... 340/608; 340/626; 340/606; 340/605; 340/618; 340/591; 417/477.1; 417/53; 417/63; 604/153; 604/156
(58) Field of Search ................................ 340/608, 626, 340/606, 605, 618, 591; 417/477.1, 53, 63; 604/153, 156

(56) References Cited

U.S. PATENT DOCUMENTS

| | | | |
|---|---|---|---|
| 4,373,525 A | 2/1983 | Kobayashi | 128/214 E |
| 4,526,574 A | 7/1985 | Pekkarinen | 604/52 |
| 4,534,756 A | * 8/1985 | Nelson | 604/505 |
| 4,617,014 A | 10/1986 | Cannon et al. | 604/67 |
| 4,690,673 A | 9/1987 | Bloomquist | 604/67 |
| 4,836,752 A | 6/1989 | Burkett | 417/12 |
| 5,217,355 A | 6/1993 | Hyman et al. | 417/474 |
| 5,395,320 A | 3/1995 | Padda et al. | 604/65 |
| 5,439,355 A | 8/1995 | Jimison et al. | 417/63 |
| 5,484,239 A | 1/1996 | Chapman et al. | 417/477.8 |
| 5,657,000 A | 8/1997 | Ellingboe | 340/608 |
| 5,759,017 A | 6/1998 | Patton et al. | 417/477.9 |
| 5,813,842 A | * 9/1998 | Tamari | 417/477.1 |
| 6,085,574 A | 7/2000 | Neftel et al. | 73/19.03 |
| 6,293,758 B1 | 9/2001 | Green et al. | 417/53 |

* cited by examiner

Primary Examiner—Daniel J. Wu
Assistant Examiner—Tai T. Nguyen
(74) Attorney, Agent, or Firm—John W. Montgomery; Haynes & Boone, LLP.

(57) ABSTRACT

A tubing installation checking device is provided for determining proper installation of a tubing along a tube receiving channel in a peristaltic pump of the type having a tube receiving channel and a door for holding a tubing therein. The tubing installation checking device includes a pressure sensor held in the peristaltic pump positioned along the tube receiving channel downstream from the pumping mechanism for sensing pressure in the tubing and for providing a signal representing the sensed pressure. A valve is provided held in the peristaltic pump along the tube receiving channel downstream from the pressure sensor for closing the tubing when it is installed in the tube receiving channel. A computer program is provided for closing the valve, for activating the pumping mechanism for a partial pumping stroke, for receiving a first pressure signal from said pressure sensor indicating the sensed pressure after the partial pumping stroke, for holding the pumping mechanism stationary during a predetermined period of time, for receiving a second pressure signal indicating the pressure in the tubing after the predetermined period of time, for comparing the first and second pressure signals to determine whether there is leakage in the tubing indicating improper tubing installation and if so for providing an alarm signal to indicate improper tubing installation.

13 Claims, 8 Drawing Sheets

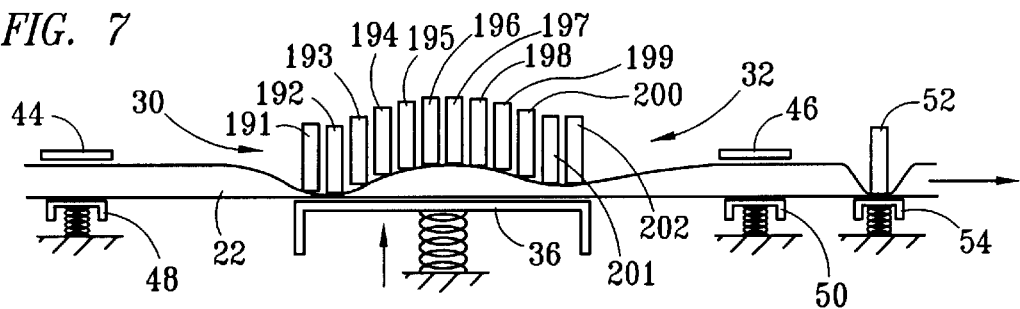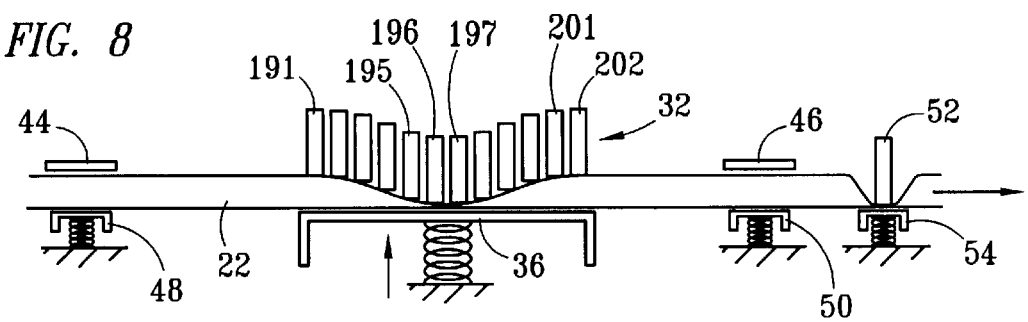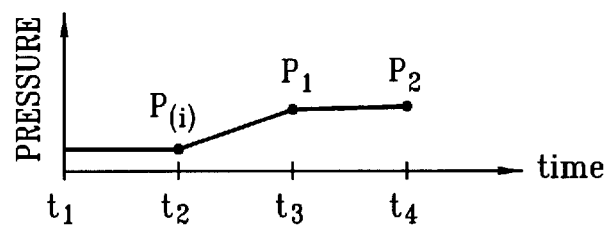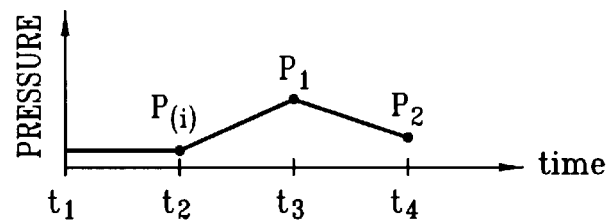

PROPER TUBING INSTALLATION TESTING METHOD AND APPARATUS FOR A PERISTALTIC PUMP

TECHNICAL FIELD OF THE INVENTION

The present invention relates to peristaltic pumps and in particular to a method and device for testing proper placement of a tubing in pumping engagement prior to operation of the peristaltic pump.

BACKGROUND OF THE INVENTION

In peristaltic infusion pumps, and in particular linear peristaltic infusion pumps, appropriate placement of a tubing upon which the pumping mechanism of the pump has in the past been a manual function accomplished by the pump operator. Accurate alignment and proper installation of the tubing has been a function of operator skill and care. Because the tubing is flexible it has been possible to insert the tubing improperly close the door or other tubing capture or holding mechanism and activate the pumping mechanism with the improperly installed or misaligned tubing. Although efforts are made to always properly insert the tubing and also to use only a proper size and pump compatible wall thickness tubing, poor alignment or installation of an improper tubing can result in a malfunction or inaccurately metered fluid flow.

SUMMARY OF THE INVENTION

A tubing installation checking device and a method is provided in a peristaltic pump having a tube receiving channel and a door for holding a tubing therein. The checking device and method are for determining proper installation of a tubing along a receiving channel canal in to which the tubing is inserted for pumping engagement with a pumping mechanism. The checking device comprises a pressure sensor held in the peristaltic pump so that the pressure sensor is positioned along the tube receiving channel downstream from the pumping mechanism for sensing pressure in the tubing and for providing a signal representing the sensed pressure. A valve is also held in the peristaltic pump along said receiving channel downstream from said pressure sensor for closing a properly installed tubing in the tube receiving channel. The method is effectively implemented by a computer program operatively coupled to the peristaltic pump for activating the valve to close off fluid flow through the tubing after the tubing is installed and the door is shut, for activating the pumping mechanism for a partial pumping stroke, for receiving a first pressure signal from said pressure sensor indicative of the sensed pressure after the partial pumping stroke, for holding the pumping mechanism stationary a predetermined period of time, and for receiving a second pressure signal indicative of the pressure in the tubing after the predetermined time period, and for comparing the first and second pressure signals to determine whether there is fluid flow leakage through the tubing. If there is leakage through the tubing, such leakage is an indication of improper tubing installation and the program activates an alarm signal to indicate such improper tubing installation.

In an enhanced version an initial pressure is sensed in the tubing as soon as the tubing is inserted, the door is shut and the downstream valve is activated to close the tube. Then the pumping mechanism is activated for a partial pumping stroke and the first pressure is measured. The initialization pressure is compared to the first pressure to see whether the first pressure is higher as expected for a properly installed tubing. If not an initial alarm signal is provided and the remainder of the testing need not be implemented. If the first pressure is higher than the initialization pressure, then the second pressure is sensed after the predetermined period. The second pressure is compared to the first pressure to determine whether there is any drop in the pressure to indicate leaking through the tubing.

The present invention provides a method and a device for testing the proper loading of tubing into a peristaltic pump. The apparatus comprises a peristaltic pump having a tubing channel and a closeable door by which a tubing is engaged in the tubing channel of the pump. A pressure sensor is positioned adjacent to the tubing downstream from the pumping fingers, and a shutoff valve is positioned for engagement against and closure of the tubing downstream from the downstream sensor. Upon engagement of the tubing and prior to pump operation, the downstream valve closes the tubing, and the pumping fingers are engaged against the tubing and moved forward, creating a trapped pocket of fluid in the tubing downstream from the pumping fingers and upstream from the closed valve. The forward movement of the pumping fingers is stopped temporarily, and the pressure of the fluid trapped in the tubing is monitored by the downstream sensor. If the pressure signal initially increases upon movement of the pumping fingers forward and then remains constant when the movement of the pumping fingers is stopped, a good seal, and therefore proper alignment of the tubing in the pumping channel, is indicated. If the sensed pressure either does not increase when the pumping fingers are moved forward or increases and then rapidly decreases, there is an indication that either the closure valve has not closed the tubing fully or the pumping fingers do not completely collapse the tubing such that a leak is detected, indicative of misalignment or improper installation of the tubing into the peristaltic pump.

BRIEF DESCRIPTION OF THE DRAWINGS

These and other benefits and inventions can be more fully understood and a better understanding of this invention can be obtained when the following detailed description of the preferred embodiments is considered in conjunction with the following drawings in which like numbers represent like elements and in which:

FIG. 7 is a schematic depiction of linear peristaltic pumping elements engaged at an initial pumping position against a tubing along a tube receiving channel;

FIG. 8 is a schematic depiction of linear peristaltic pumping elements as in FIG. 7 with the pumping elements advanced a few steps of pumping compression against the tubing from the initial position shown in FIG. 7;

FIG. 9 is a graphical depiction of pressure sensed in a tubing properly installed in a peristaltic pump, downstream from the pumping elements and upstream from a closed valve as a function of time during testing for proper tubing installation according to one embodiment of the invention;

FIG. 10 is a graphical depiction of pressure sensed in the tubing improperly installed in a peristaltic pump, downstream from the pumping elements and upstream from a closed valve as a function of time during testing for proper tubing installation according to one embodiment of the invention;

DESCRIPTION OF THE PREFERRED EMBODIMENTS

Figure 1:
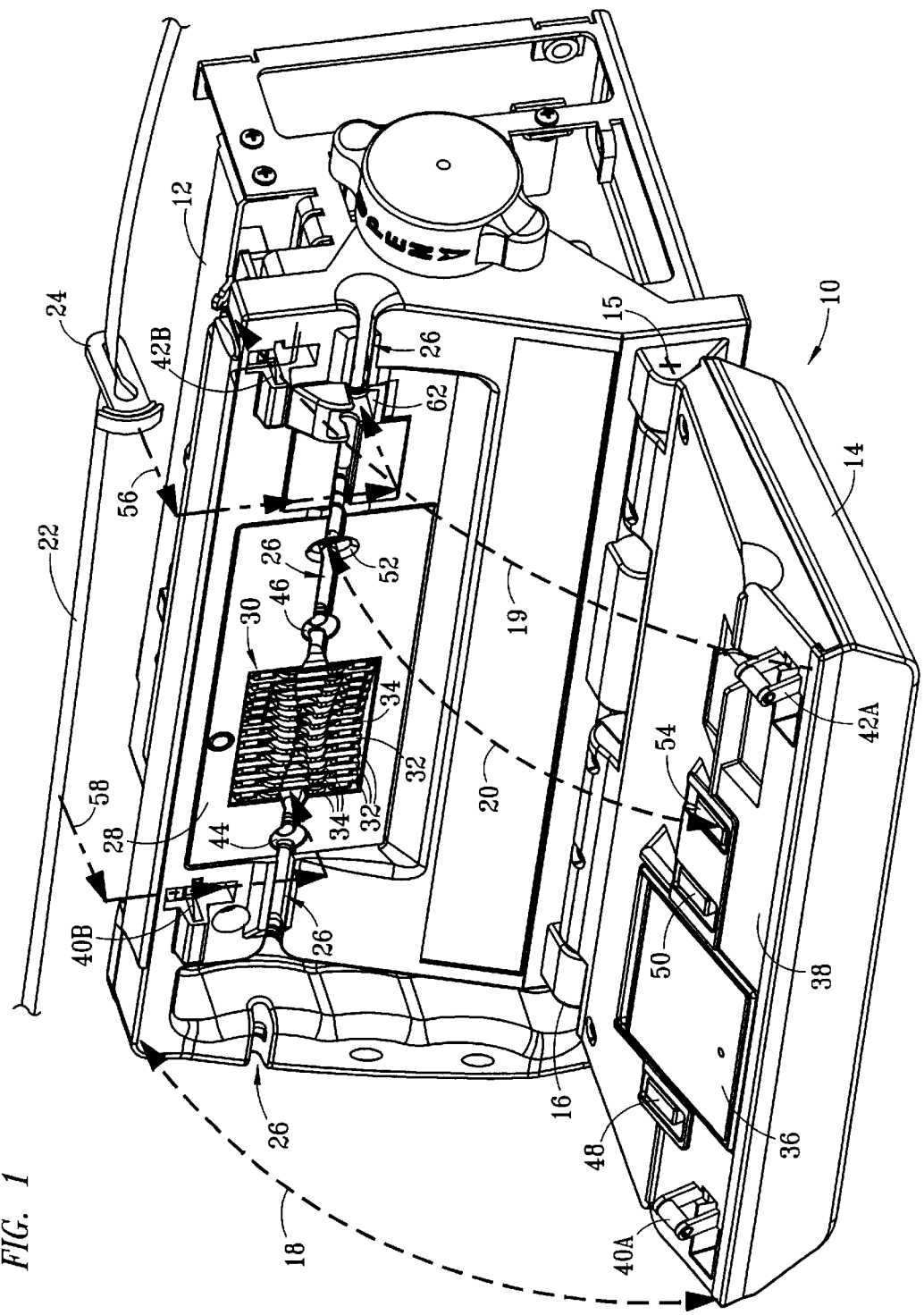
FIG. 1 is a perspective view of a peristaltic pump of a type for which the present invention may be applicable, in this figure a linear peristaltic pump and a tubing to be installed are depicted.

FIG. 1 shows a perspective view of one embodiment of a peristaltic pump according to the present invention and in particular a linear peristaltic pump 10. The pump 10 as depicted includes a pump body 12 having a door 14 pivotally attached as at hinges 15 and 16, for closing against an interior face 28 of the pump body 12 as shown with assembly arrows 18, 19 and 20. A flexible tubing 22 is depicted having a slide clamp 24 engaged there along to prevent fluid flow while tubing 22 is outside of the pump 10. Tubing 22 is to be installed by placing it in and along an engagement pathway or tube receiving channel 26. Tube receiving channel 26 is formed along the interior face 28 of the pump body 12. The slide clamp 24 is inserted (as shown with assembly line 56) into automatic clamp mechanism 62 by which the slide clamp 24 is released and the pump controls opening and closing flow in tubing 22. A pumping mechanism 30, that includes in this embodiment an assembly of linear peristaltic pumping elements 32 and reshaping fingers 34, is mounted in the pump body 12 positioned along channel 26 for receiving and for acting upon the tubing 22 in pumping engagement. It will be noted that the reshaping fingers 34 are the subject of another patent and though beneficial for reshaping the tubing during pumping operation, are not specifically required for the operation of the current invention.

When the tubing 22 is manually inserted into channel 26 (as shown by assembly line 58), the door 14 is closed shut as by pivoting about hinges 15 and 16 and latched against interior face 28. The door 14 functions as a tubing holder to capture and hold the tubing 22 into channel 26. Also shown is a retractable spring loaded platen 36 formed into and movably attached to the inside face 38 of door 14. When door 14 is shut, platen 36 is positioned adjacent to the pumping mechanism 30 and is pushed by spring action against interior face 28. Thus the platen 36 provides both the indicated tubing holding function and also provides a backing support surface for the pumping mechanism 30. Door 14 may be latched into a closed position using latches 40A, 40B, 42A and 42B. Also an upstream pressure sensor 44 and a downstream pressure sensor 46 are positioned and attached to the pump 10 along the channel 26, on either side of the pumping mechanism 30. Upstream and downstream are determined with respect to the pumping direction of flow to the patient and the position of the sensor (or the valve as the case may be) relative to pumping mechanism 30. Also held in door 14 are spring loaded pressure sensor supports, including upstream pressure sensor support 48 and downstream pressure sensor support 50. According to the invention and as depicted in the embodiment of FIG. 1, there is a downstream valve 52 for selectively closing or opening fluid flow through the tubing 22. The downstream valve 52 is downstream from both the pumping mechanism 30 and from the downstream sensor 46. A spring loaded valve backing plate 54 is provided correspondingly positioned opposite from valve 52 at the inside face 38 of door 14. The operation of the pressure sensors 44 and 46 and the operation of the valve 52 will be more fully discussed below.

Figure 2:
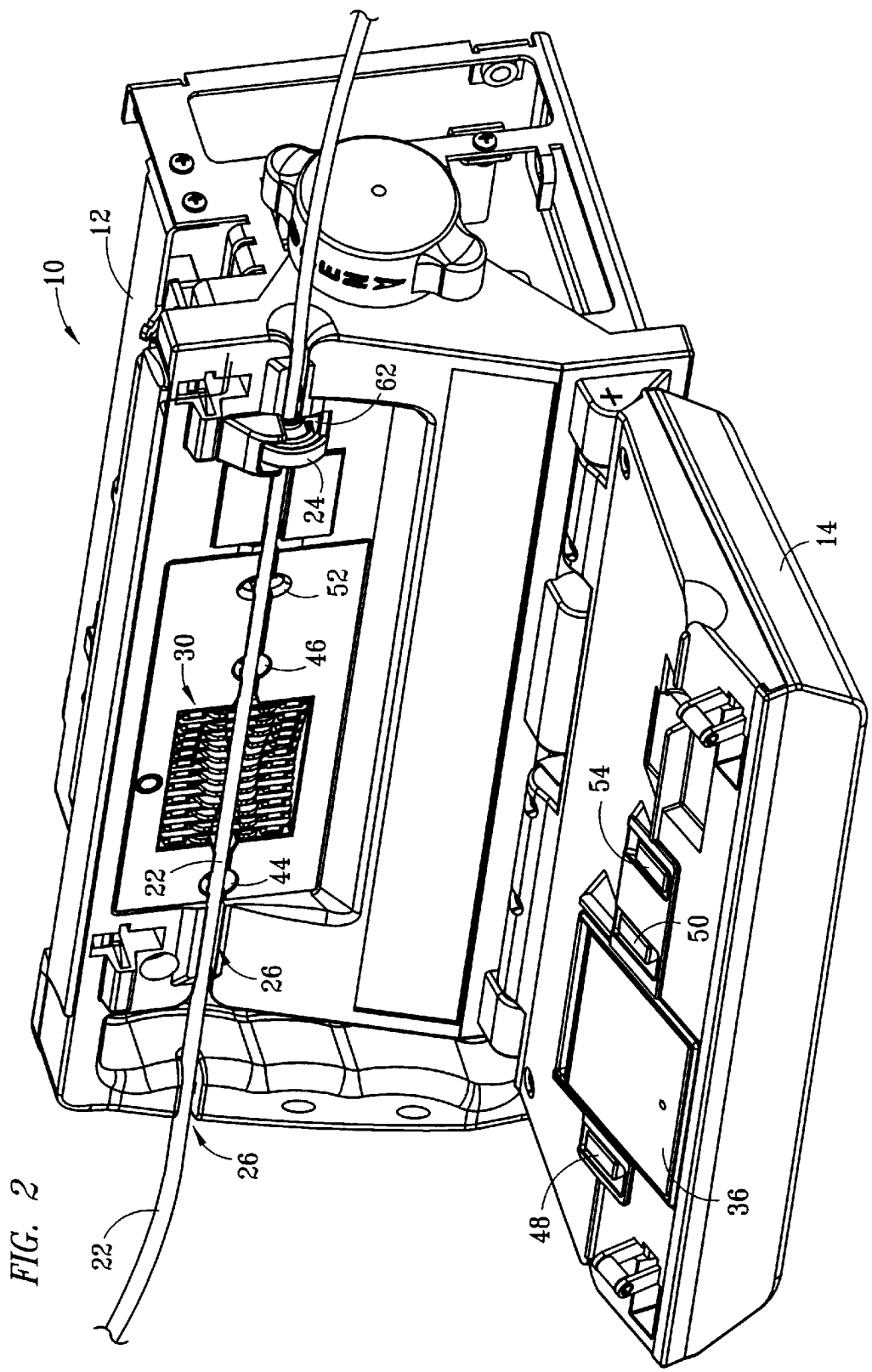
FIG. 2 is a perspective view of the pump of FIG. 1 with the tubing shown properly inserted into the tube receiving channel ready for the door to be shut thereby retaining the tubing in proper installation.

FIG. 2 depicts the pump of FIG. 1 with the tubing 22 shown properly inserted into the tube receiving channel 26 ready for the door 14 to be shut thereby retaining the tubing in proper installation for pumping engagement with pumping mechanism 30 and for proper operation with valve 52 and pressure sensors 44 and 46.

Figure 3:
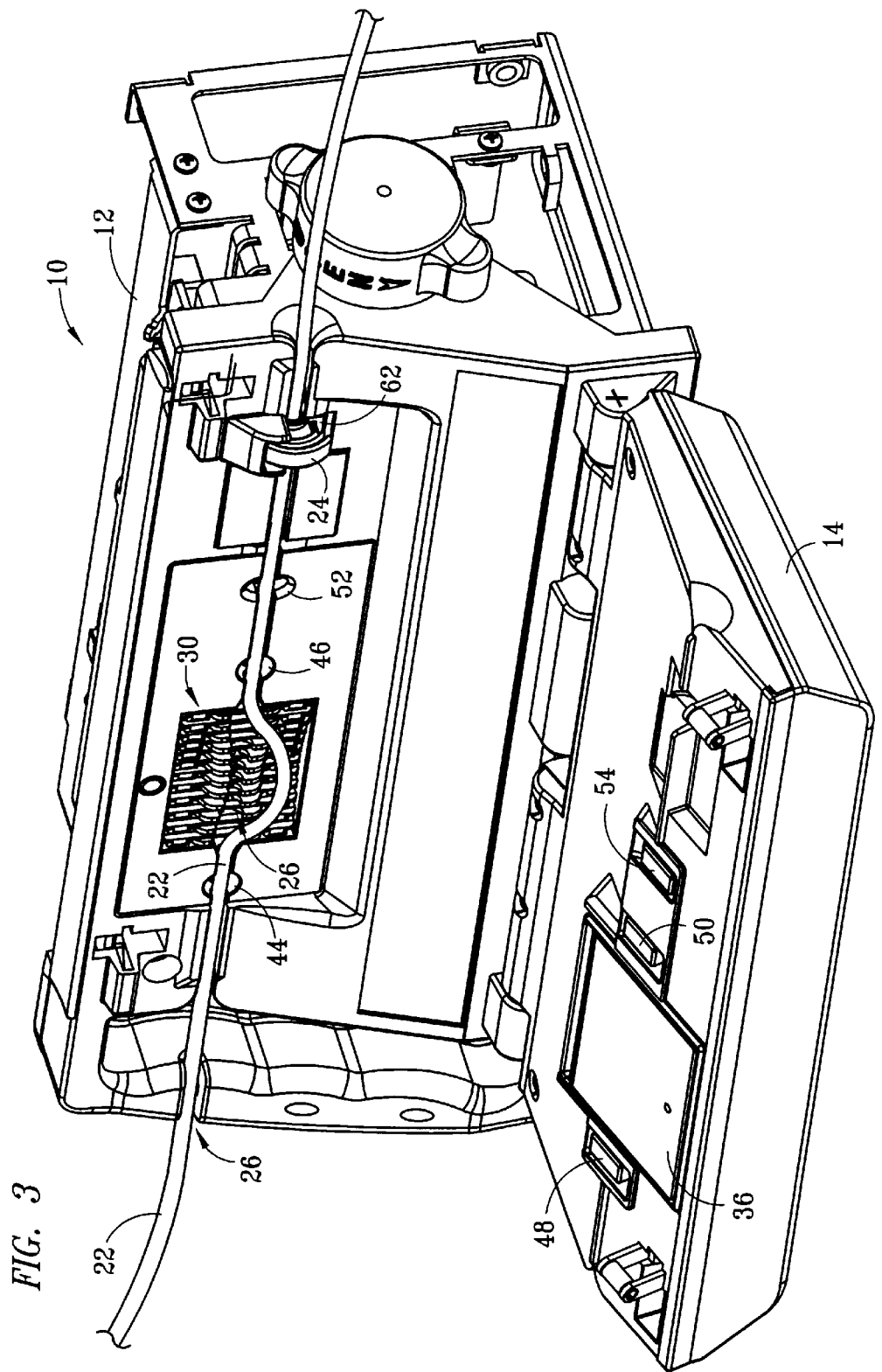
FIG. 3 is a perspective view of the pump of FIG. 1 with the tubing shown improperly inserted into the tube receiving channel prior to the door being shut whereby the tubing would be held in a position improper for pumping engagement.

FIG. 3 is a perspective view of the pump 10 of FIG. 1 with the tubing 22 shown improperly inserted and partially out of the tube receiving channel 26 prior to the door 14 being shut, whereby the tubing 22 would be improperly installed as it would be held in a position that is not proper for pumping engagement. In this depiction of an improperly installed tubing 22, such tubing 22 is shown out of tube receiving channel 26 at a portion of its length adjacent to pumping mechanism 30. It will be understood that the flexible tubing 22 might also be outside of channel 26 elsewhere along its length. It might also be understood that tubing 22 might be kinked. Further it will be understood that an improper installation might include installing a tubing 22 that was too small in diameter or that had a wall thickness that was too thin or a wall thickness that was too thick for proper pumping engagement. All of these and other improper installations of tubing into a peristaltic pump might be detected according to the present invention.

Figure 4:
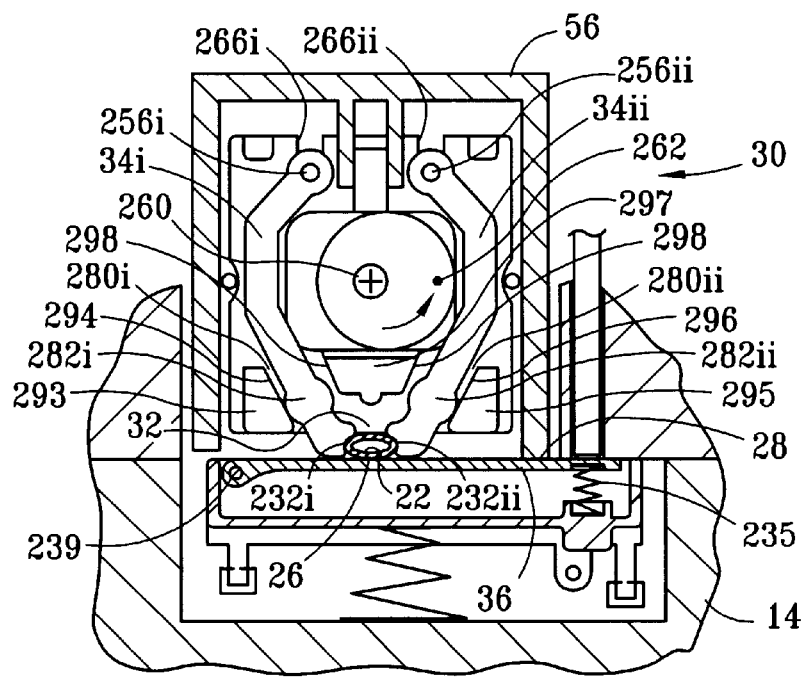
FIG. 4 is a schematic partial cross-sectional view through the pumping mechanism showing a pumping element in relation to a tubing partially compressed against a retractable platen held in a shut door.

FIG. 4 depicts a schematic partial cross-sectional view of pumping mechanism 30 in relation to a tubing 22 partially compressed against the retractable platen 36 held in door 14. One of a plurality of pumping elements 32, is shown in this embodiment as a reciprocally moveable rectangular shaped plate. According to this embodiment of the invention applied to a linear peristaltic pump 10, pairs of reshaping fingers 34$i$ and 34ii are shown pivotal attached and activatable into and out of reshaping contact with the tubing 22. The reciprocal movements of adjacent pumping elements 32 activate the reshaping contact. The reciprocation position of the pumping element 32 in FIG. 4 corresponds generally to a position with pumping element 32 partially compressed against tubing 22. The amount of compression is controlled according to the rotation position 297 of cam lobe 262. It can be seen that pumping element 32 has a flat top surface 230. Flat top surface 230 is parallel to the backing support surface provided by platen 36.

It will be understood that a plurality of side by side pumping elements 32 are aligned along the tube receiving channel 26 and are activated by a plurality of corn lobes driven by a cam shaft 260. Each cam lobe 262 is off-set from the next cam lobe sequentially compress tubing 22 against platen 36 to force fluid there through. The fluid is moved ahead of the sequentially compressing pump elements 32 in a direction downstream from the portion of the tubing 22 that at any given time is fully compressed by at least one of the pumping elements 32. Behind the fully compressed portion of the tubing 22, the pumping elements 32 sequentially retract to allow new fluid to enter into the tubing 22. The reshaping fingers 34i and 34ii are shown in a position partially engaged with the sides of flexible tubing 22. The respective reshaping jaws 232i and 232ii contact and reshape the tubing 22 as pumping elements 32 retract from compressing the flexible tubing 22. This motion of the reshaping fingers 34i and 34ii is automatically accomplished using projection 293 having angled surface 294 and projection 295 having angled surface 296 formed on pumping element 32. A third projection 297 centrally located on pumping element 32 provides angled surface 298 and angled surface 299. The projections 293, 295 and 297 have approximately the same thickness as reshaping fingers 34i and 34ii and with their angled surfaces together form actuator channels 280i and 280ii which act against portions 282i and 282ii of reshaping fingers 34i and 34ii. Thus reshaping fingers 34i and 34ii are pivoted on pivot connector rods 256i and 256ii as the next adjacent pumping element 32 reciprocates compressing tubing 22 and retracting from tubing 22 in pumping action. The pumping element 32 shown in FIG. 4 is one of a plurality of pumping elements 32 and corresponding sets of reshaping fingers 34 held in the pumping assembly 30 within rectangular housing 56. The pumping element 32 also has slots 266i and 266ii formed to accommodate guided reciprocal motion relative to the connection pivot rods 256i and 256ii.

Figure 5:
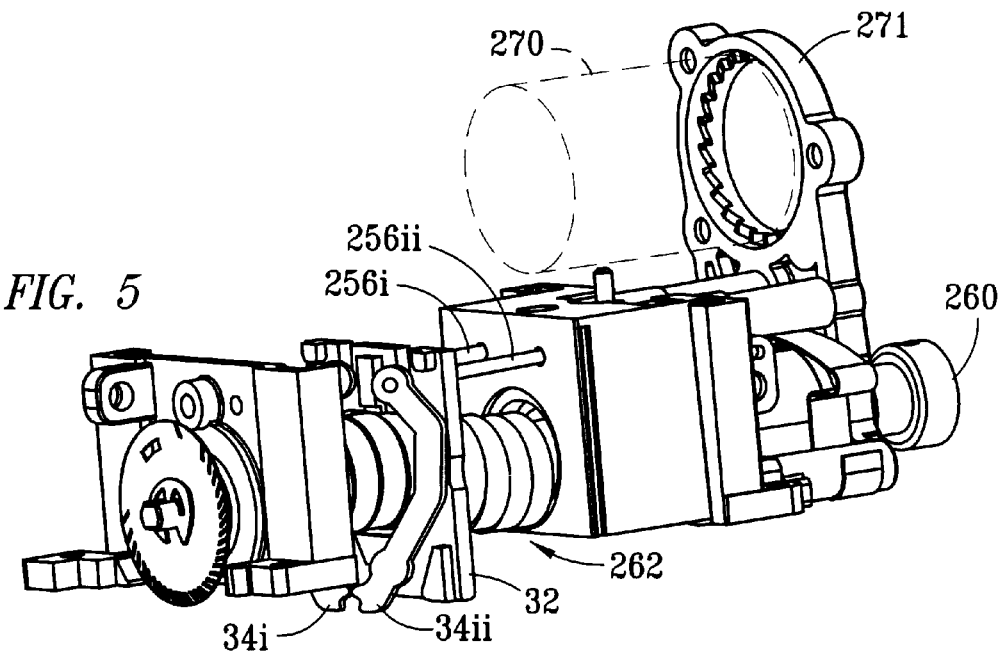
FIG. 5 is a schematic perspective view depicting a partially constructed pump cam shaft with all of the plurality of pumping elements and reshaping fingers removed except one set for clarity.

Other features of construction maybe further understood with reference to the schematic prospective view in FIG. 5 depicting a portion of pump 10 including a camshaft 260, a mount 271 for motor 270, one of the plurality of pumping plates 32 and one pair of the plurality of reshaping fingers 34 attached along connection rods 256i and 256ii. The other structure comprising pump 10 has been removed from view in FIG. 5 for clarity of understanding.

Figure 6:
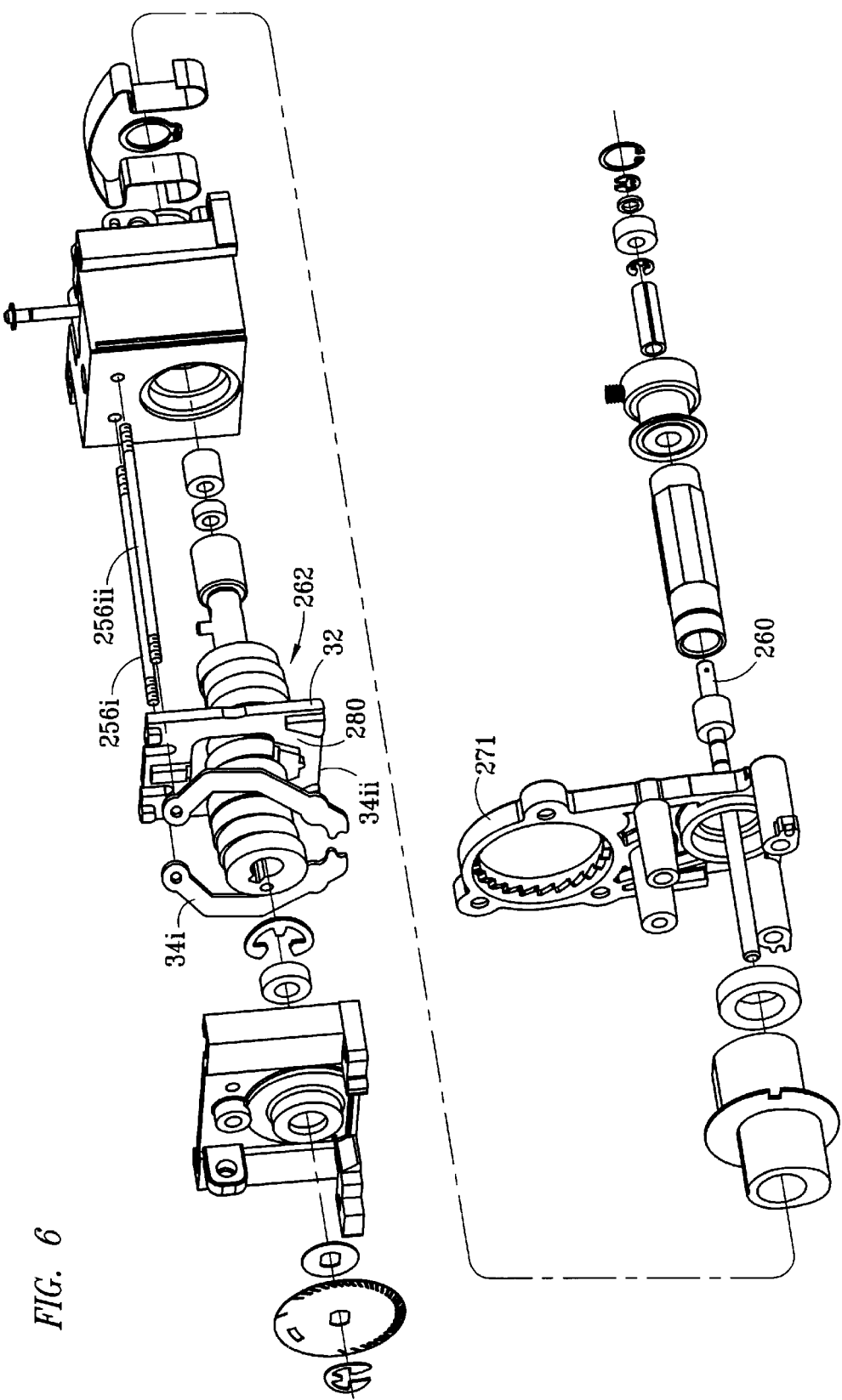
FIG. 6 is a schematic exploded construction view depicting the partially constructed pump assembly of FIG. 5, again with all of the plurality of pumping elements and reshaping fingers removed except one set for clarity.

Further details of the structure according to FIG. 5 may also be understood with reference to FIG. 6. FIG. 6 is a schematic exploded assembly view of that portion of the pump 10 that is depicted in FIG. 5. Again the multiple pumping elements and reshaping fingers are represented with only one set for clarity. It will be understood that each of the plurality of cam lobes 262 will engage a pumping element 32 and a corresponding set of reshaping fingers 34i and 34ii.

It has been found that before pumping operation is activated it is desirable to run the inventive proper tubing installation testing method and certain other initial tests. For purposes of demonstrating the inventive test to determine whether the tubing 22 is properly installed, reference may be had to both FIG. 4 and FIG. 7. In FIG. 7 a portion of the components of a linear peristaltic pump are schematically depicted as they engage the tubing 22. In this view the plurality of pumping elements 32 comprise twelve pumping elements that are separately labeled with reference numbers 191 through 202. As an advantageous starting point for such initialization test, the cam lobes 262 are rotated to a position for initiation of a pumping stroke. This position is shown in FIG. 7 with pumping elements 192 and 193 in the full pumping extension so that elements 200 and 201 are open and pumping elements 192 and 193 are closed. The tubing 22 is loaded into the tube receiving channel 26, the door 14 is shut, as shown in FIG. 4. The downstream valve 52 remains closed or is activated to a closed position and the platen 36 is extended to abut against tubing 22 in a pumping position. The platen 36 is biased by spring 235 into its pumping engagement position against the interior face 28 of door 14. Such an initial pumping position is schematically depicted in FIG. 7.

In one embodiment of the invention, the pumping mechanism 30 is moved forward a few degrees of rotation or a portion of a step or a few steps of pumping element compression, as schematically depicted in FIG. 8. As shown schematically in FIG. 8, pumping elements 194 and 195 become fully extended compressing against tubing 22 if it is properly installed. Although the pumping elements are advanced forward a significant amount in the schematic depiction of FIG. 8 (corresponding to about 60 to 90 degrees of rotation), it will be understood that the actual amount of forward rotation may be a much smaller amount depending upon the sensitivity of the sensor 42 and so that the pumping mechanism is not damaged by an excessive amount of pressure build-up in tubing 22. A first test pressure P1 is advantageously sensed as soon as the predetermined forward rotation is stopped. The pumping mechanism is then held without rotation for a predetermined length of time and a second test pressure P2 is sensed at the downstream pressure sensor 46. The magnitude of the first pressure P1 is compared to the magnitude of the second test pressure P2. If there is leakage through the tubing 22 at either the pumping mechanism 30 or at the valve 52, the second test pressure P2 will be lower than the first test pressure P1, thereby indicating improper tubing installation. An alarm will be activated if the first test pressure P1 and the second test pressure P2 are found to be different. If the first and second test pressures P1 and P2 are the same, there is no indication of an improper tubing installation.

In another embodiment, after the tubing 22 is loaded, the door 14 is shut, the platen 36 is extended, and the downstream valve 52 is closed, an initial short time period may be permitted to allow the pressure to stabilize. The initial pressure P(i) in tubing 22 is then sensed at downstream sensor 46 after the short time period for stabilization. This may be further understood referring to FIG. 9, which is a graphical depiction of the sensed test pressure measurements as a function of time. The initial time period to allow pressure to stabilize is shown as the period from t1 to t2. An initialization test pressure is then sensed in the tubing 22 by sensor 46 at time t2. This initialization test pressure corresponds to the pressure P(i) shown at t2 in FIG. 9. After the initialization test pressure P(i) is sensed at t2, the pump is then rotated forward a few degrees of rotation (again represented by several steps of pumping element compression) during a period of time t2 to t3 shown in FIG. 9. The pumping mechanism 30 is then stopped. Again, as shown schematically in FIG. 8, pumping elements 194 and 195 are fully extended compressing against tubing 22. The first test pressure P1 is advantageously sensed at t3 as soon as the predetermined forward rotation is stopped.

In this embodiment a first test pressure P1 is sensed at t3 and is compared to the initialization pressure P(i) to determine whether the first test pressure P1 is higher than the initialization pressure P(i). Where the tubing is properly installed there will be a pressure build-up between the pumping elements and the closed downstream valve 52. If the first test pressure P1 is not higher than initialization pressure P(i), an alarm is signaled, to indicate at least one condition of improper tubing installation. For example if the tubing 22 is positioned entirely outside of the tube receiving channel 26 so that either the pumping mechanism 30 does not engage the tubing or the valve 52 does not engage the tubing, a pressure increase from time t2 to time t3 might not be sensed. When there is no sensed pressure increase resulting from the partial forward pump rotation, an alarm is signaled and the test may be stopped to allow the operator to correct the improper installation.

If the first test pressure P1 at t3 is higher than the initialization pressure Pi at t2, the test continues to determine whether another improper installation condition exists. The pumping mechanism is then held without rotation for another predetermined length of time t3 to t4. At time t4, a second test pressure P2 is sensed at the downstream pressure sensor 46. The magnitude of the first pressure P1 is compared to the magnitude of the second test pressure P2. If the tubing is properly installed there will be no leaking and the pressure will hold so that P2 will be equal to P1 as shown in FIG. 9. If the first and second test pressures are the same there is no indication of an improper installation. If there is a leak at either the pumping mechanism or at the valve 52, the second test pressure will be lower than the first test pressure indicating improper tubing installation as shown graphically in FIG. 10. Thus an alarm will be signaled if the first test pressure P1 and the second test pressure P2 are found to be different.

In yet another embodiment, the pressure in the tubing 22 maybe continuously monitored over the test time periods. When the monitored pressure is stabilized, the pumping mechanism may be advanced. If the monitored pressure increases either after a predetermined amount of forward pump rotation or after a predetermined increase in the monitored pressure, the rotation can be stopped. the pressure continues to be monitored. If there is no increase in the monitored pressure, an alarm may be signaled to indicate improper tubing installation and to allow correction. If pump rotation is stopped without an alarm signal the pressure continues to be monitored either over a predetermined period of time to determine if a constant pressure is maintained or until there is a sufficient drop in the monitored pressure to indicate a leak and thus to indicate improper installation of the tubing. If the pressure does not hold, an alarm will be signaled to indicate the improper installation condition and to allow the operator to correct the condition before pumping continues. Thus, by monitoring the pressure continuously over the test period, the total time required to find an improperly installed tubing condition might be shortened where a significant amount of leakage is detected very quickly.

Figure 11:
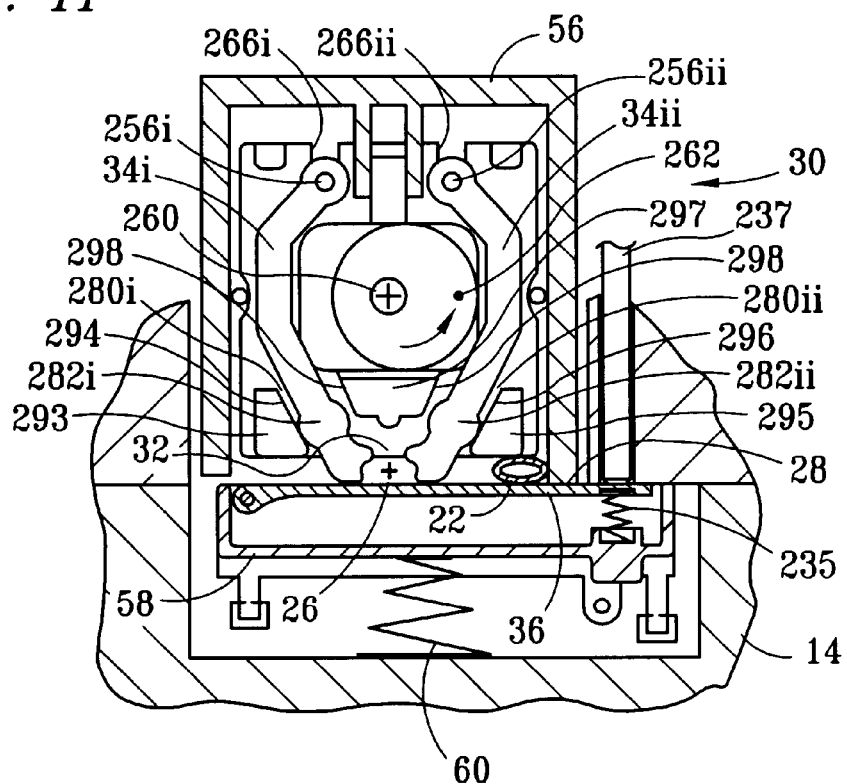
FIG. 11 is a schematic partial cross-sectional view depicting one possible improper tubing installation scenario where the tubing is outside of the tube receiving channel at the pumping mechanism.

One example of a misaligned tubing 22 is depicted in the perspective view of FIG. 3 and a corresponding side cross-sectional view FIG. 11. In the instance of such misalignment the tubing position may be such that the platen 36 is held away from its proper position against the interior face 28 when the door 14 otherwise appears to be properly closed. In this situation the pumping elements 32 would not fully collapse the tubing 22. In an alternative example of an improperly loaded tubing, the valve 52 might not fully close the tubing. In either of these situations, leakage through the tubing should be indicated by the inventive testing mechanism and method. If there is a large amount of leakage or if the sensor 46 is not in contact with the tubing, the pressure will not increase significantly from a first test pressure P1 to a higher second test pressure P2. If there is only a small amount of leakage through the tubing 22 at either the pumping elements 32 or at the valve 52, a significantly higher second pressure P2 might be reached, however the higher pressure will not be held steady for any significant amount of time. Thus, if P1 is approximately equal to P2 or if P2 decreases during the holding period, an alarm will be sounded, and the pump will be inactivated until the improper installation of the tubing is corrected.

In a situation where a tubing is too large, the improper size will likely be noticed before the door is closed because the size of channel 26 will not allow a significantly larger tubing to be inserted. If the tubing is small enough to fit into the channel 26 yet too large to allow proper closure by valve 52 or by pumping elements 32, the inventive proper tubing installation testing device and method will detect leakage. If the tubing is much too small it might also be noticed visually or it will be seen that no pressure will be built up during the proper installation pressure testing sequence. In the situation where the tubing is only slightly too small, or the wall thickness is not compatible with the pumping mechanism, the last part of the proper installation test will likely fail because the tubing will not be fully collapsed by either the valve 52 or by the pumping elements 32. Thus, the second test pressure P2 will not hold during the last part of the test. Such a situation will not be correctable by simply realigning the tubing and the operator, after a repeated failure of the proper installation test, may be prompted to check the tubing size.

Figure 12:
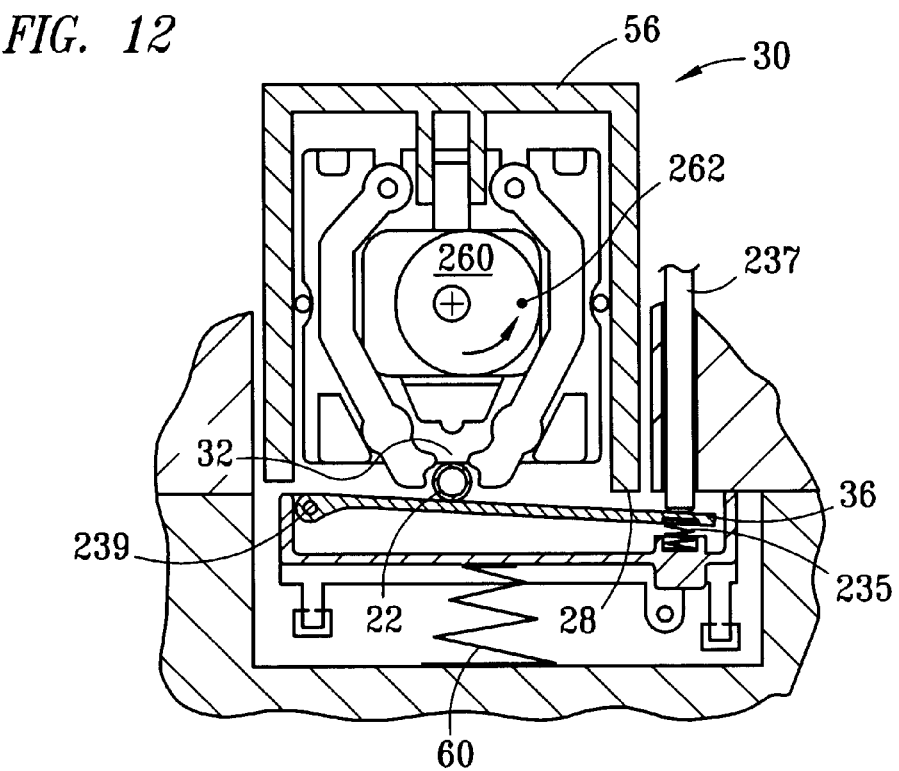
FIG. 12 is a schematic partial cross-sectional view, similar to FIG. 4, showing a retractable platen in a position retracted against a spring through the actuation of retraction rod.

In an additional calibration stage, preferably with the knowledge that the tubing 22 is properly installed as determined above, the upstream pressure sensor 44 should be calibrated to the downstream pressure sensor. To do this, the tubing 22 should be completely open and not compressed by the pumping elements. FIG. 12 depicts a schematic partial cross-sectional view similar to FIG. 4 showing retractable platen 36 in a position retracted against spring 235 through the actuation of retraction rod 237. The retraction rod 237 acts against one end of platen 36 with an opposite end of platen 36 pivotally connected at 239 to door 14. Thus, retraction rod 237 pushes platen 36 off of flexible tubing 22. It is noted that platen 36 is pushed off of tubing 22 regardless of the pumping position of cam lobes 262 or the position of any of the plurality of pumping plates 32. Platen 36 is pushed or lifted a sufficient distance to allow flexible tubing 22 to become open through the resilience of flexible tubing 22. Platen 36 is also a part of a slidable platen safety housing 58 that is strongly biased to a desired position, as with bias spring 60. If the magnitude of force on the platen 36 is too large and greater than the amount of force require for complete compression of spring 235, then damage is avoided by sliding movement of the platen into the safety housing 58 against the strong bias spring 60.

Figure 13:
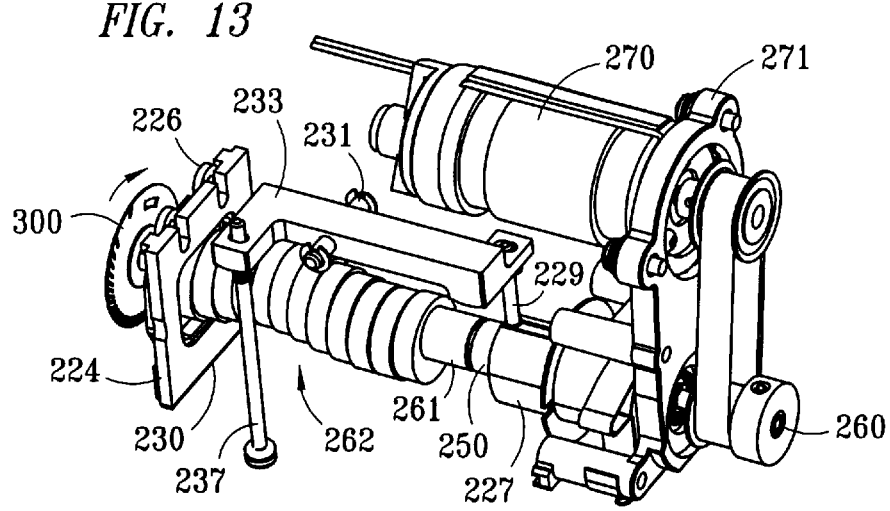
FIG. 13 is a perspective view of a partially constructed cam shaft assembly with the pumping elements removed to show a platen lift cam and retraction rod.

FIG. 13 schematically depicts the pumping camshaft 260 and the drive motor 270 as well as the platen 36, the actuating rod 237 and a platen lifting assembly. The platen lifting rod 237 is connected to a lever 233 that pivots at 231 in response to a cam follower 229 actuated by a lift cam 227. Lift cam 227 is mounted through a one-way clutch assembly 250 to camshaft 260. Thus reverse rotation of motor 270 is required to engage clutch 250 and thereby rotate lift cam 227. Similarly cam lobes 262 are mounted to cam 260 through a one-way clutch mechanism 261 that engages only in the forward motor rotation direction, (opposite direction from engagement of clutch 250). Thus, reverse rotation to engages clutch 250 and disengages rotation of cam shaft 260 and cam lobes 262.

Figure 14:
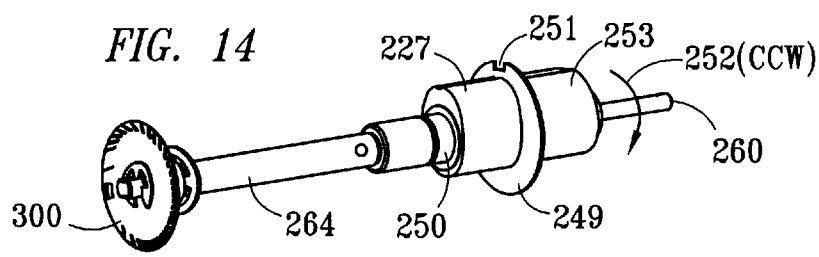
FIG. 14 is a perspective view of a cam shaft schematically depicting cam rotation for positioning various cam lobes in positions for testing and/or initial calibration prior to pumping operation.

The purpose of retracting platen 36 is, in part, to calibrate the pump signals from sensors 44 and 46 as will be more fully understood with reference to FIGS. 13 and 14. FIG. 14 is a schematic perspective depiction of the camshaft 260 with a lifting cam 227 as well as lifting cam index wheel 249 and volume equalization timing wheel 300. For purposes of clarity of explanation, the convention will be adopted herein to consider forward motor rotation as counter-clockwise rotation viewing the camshaft 260 from the left hand side of FIGS. 13 and 14. According to this convention the pumping cam lobes 262 are driven with counter-clockwise rotation of motor 270 and of camshaft 260 and the platen lifting cam 227 is driven with clockwise rotation of motor 270 and correspondingly camshaft 260. In FIG. 14 the rotation arrow 252 depicts clockwise rotation. Preferably, when the pump is initially started, and each time the door 14 is opened and then shut, an automatic initialization procedure is undertaken including testing for proper tubing installation and then calibration of the pressure sensors 44 and 46. This will include clockwise rotation of cam 260, engaging clutch 250, and rotating platen cam 227 until the index notch 251 of index wheel 249 is in a proper position for raising cam follower 229 thereby actuating lever arm 233 to pivot lift actuator 237 against platen 36. In FIG. 14 clockwise rotation as a arrow 252 causes clutch 250 to engage platen cam 227. Clockwise rotation continues only until notch 251 of index wheel 249 is located at the proper platen liftoff position.

Figure 15:
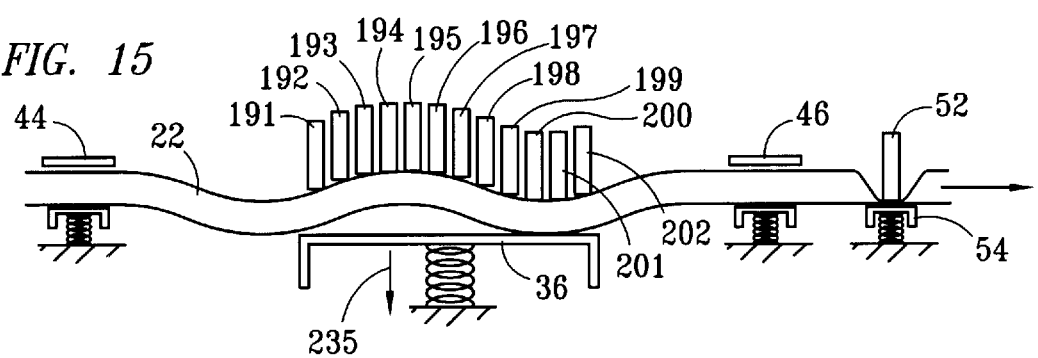
FIG. 15 is a schematic depiction of pumping elements and platen lifted off from contact with the tubing for initial calibration of upstream and downstream pressure sensors.

FIG. 15 schematically depicts a lifted platen 36 so that tubing 22 is opened entirely along the pumping mechanism. The tubing 22 is released regardless of the position at which the operation was stopped. Thus, for example as in FIG. 15 where the pumping plates 200 and 201 are in a down position so that tubing 22 would normally be closed if platen 36 was not lifted, the tubing 22 becomes opened as shown. With the platen 36 lifted, the valve 52 is also brought to a closed position pushing against spring loaded back plate 54. With the tubing 22 closed downstream from both pressure sensors 44 and 46 and with the tubing 22 opened there between, the pressure inside of tubing 22 corresponds to the upstream pressure normally determined by the head height of a medical solution bottle or reservoir (not shown). Pressure sensors 44 and 46 may be constructed as strain gauge sensors such that the pressure inside of flexible tubing 22 corresponds to the expansion or contraction of tubing 22 relative to its normal size due to increased or decreased pressure of the fluid inside. With backing plates 48 and 50 biased against fixed surfaces on the face 28 of pump 10, the expansion of tubing 22 due to internal pressure maybe accurately measured with sensors 44 and 46. By equalizing the pressure inside of tubing 22 at both the upstream pressure sensor 44 and at the downstream sensor 46 and without any pumping action taking place, the sensory input from 44 may be equalized with the sensory input of 46. Thus the operational relative pressure detected after the initial equalization will be accurately reflected both with respect to upstream sensor 44 and downstream sensor 46.

Reverse direction rotation is initiated in camshaft 260 such that a clutch is engaged for forward (counter-clockwise) rotation of camshaft 260. Thus, through the use of a timing wheel 300 and appropriate one direction clutches, the cam lobes 262 can be conveniently brought to desired positions for testing proper tubing installation and for calibration of the pressure sensors.

Figure 16:
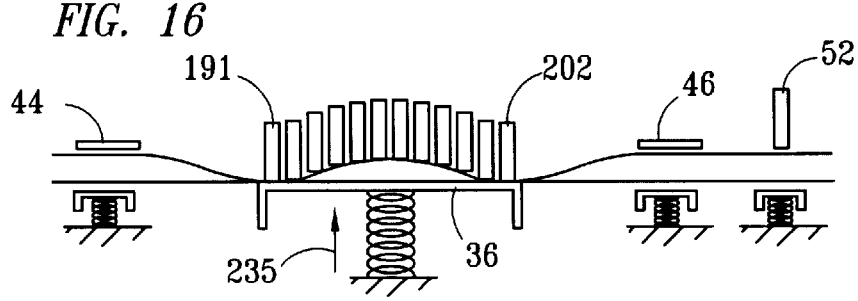
FIG. 16 is a schematic depiction of pumping elements and patent advanced against a tubing in a position for beginning pumping operation.

When the installation testing and the sensor calibration is completed, to begin pumping the mechanism is moved in reverse the final quarter of rotation. Thus, to initialize pumping the motor 270 rotates again in a reverse direction about ninety degrees of rotation so that platen lift cam 227 and downstream valve cam 52 both move to the opposite positions as shown in FIG. 16. This advances the platen 36 against tubing 22 so that platen 36 abuts by strong spring tension against face 28. Also downstream valve 52 is opened through the action of cam 253 so that tubing 22 is open downstream from the pumping mechanism 30 and fluid pumping may begin.

Other alterations and modifications and equivalents of the invention and its elements will likewise become apparent to those of ordinary skill in the art upon reading the present disclosure, and it is intended that the scope of the invention disclosed herein be limited only by the broadest interpretation of the appended claims to which the inventors are legally entitled.

What is claimed:

1. In a peristaltic pump having a tube receiving channel and a door for holding a tubing therein, a tubing installation checking device for determining proper installation of a tubing along a tube receiving channel in to which the tubing is inserted for pumping engagement with a pumping mechanism, said tubing installation checking device comprising:

(a) a pressure sensor held in the peristaltic pump positioned along the tube receiving channel downstream from the pumping mechanism for sensing pressure in the tubing and for providing a signal representing the sensed pressure;

(b) a valve held in the peristaltic pump along said tube receiving channel downstream from said pressure sensor for closing the tubing when it is installed in the tube receiving channel; and (c) a computer program for closing said valve, for activating the pumping mechanism for a partial pumping stroke, for receiving a first pressure signal from said pressure sensor indicating the sensed pressure after the partial pumping stroke, for holding the pumping mechanism stationary during a predetermined period of time, and for receiving a second pressure signal indicating the pressure in the tubing after the predetermined period of time, and for comparing the first and second pressure signals to determine whether there is leakage in the tubing indicating improper tubing installation and if so for providing an alarm signal to indicate improper tubing installation.

2. A tubing installation checking device as in claim 1 further comprising an alarm connected to the program to receive the alarm signal indicating improper tubing installation and for activation of a human perceivable alarm upon receipt of said alarm signal indicating improper tubing installation.

3. A tubing installation checking device as in claim 1 wherein said downstream pressure sensor comprises a strain gage positioned in the peristaltic pump for contacting against an outside surface of the tubing when it is installed in the tube receiving channel.

4. A tubing installation checking device as in claim 1 wherein first electronic data representing said first sensed pressure signal is stored at least temporality by said computer program for comparison with second electronic data representing said second sensed pressure signal.

5. A tubing installation checking device in a peristaltic pump having a tube receiving channel and a door for holding a tubing therein, said tubing installation checking device for determining proper installation of a tubing along a tube receiving channel canal in to which the tubing is inserted for pumping engagement with a pumping mechanism in the peristaltic pump, and said tubing installation checking device comprising:

(a) a pressure sensor held in the peristaltic pump positioned along the tube receiving channel downstream from the pumping mechanism for sensing pressure in the tubing and for providing a signal representing the sensed pressure;

(b) a valve held in the peristaltic pump along said receiving channel downstream from said pressure sensor for closing a properly installed tubing in the tube receiving channel; and (c) a computer program for closing said valve, for receiving an initialization pressure signal from said sensor upon shutting the door indicating an initialization pressure in the tube, for activating the pumping mechanism for a partial pumping stroke, for receiving a first pressure signal from said pressure sensor indicating the sensed pressure after the partial pumping stroke, for holding the pumping mechanism stationary a predetermined period of time, and for receiving a second pressure signal indicating the pressure in the tubing after the predetermined time period, and for comparing the initialization, first and second pressure signals to determine whether there is leakage in the tubing indicating improper tubing installation and if so for providing an alarm signal to indicate improper tubing installation.

6. A tubing installation checking device as in claim 5 further comprising an alarm connected to the program to receive the alarm signal indicating improper tubing installation and for activation of a human perceivable alarm upon receipt of said alarm signal indicating improper tubing installation.

7. A tubing installation checking device as in claim 5 further comprising an alarm connected to the computer program to receive an initial alarm signal upon comparison of the initial pressure sensor signal to the first pressure signal indicating that the first pressure is not a predetermined amount greater than the initial pressure to thereby indicate improper tubing installation and for activation of a human perceivable alarm indicating improper tubing installation.

8. A tubing installation checking device as in claim 5 further comprising an alarm connected to the computer program to receive an alarm signal upon comparison of the first pressure sensor signal to the second pressure signal indicating that the second pressure is at least a predetermined amount less than the first pressure to thereby indicate improper tubing installation and for activation of a human perceivable alarm indicating improper tubing installation.

9. A tubing installation checking device as in claim 5 wherein said downstream pressure sensor comprises a strain gage positioned in the peristaltic pump for contacting against an outside surface of the tubing when it is installed in the tube receiving channel.

10. A tubing installation checking device as in claim 5 wherein initialization electronic data representing the initial sensed pressure signal is stored at least temporarily for comparison with first electronic data representing said first sensed pressure signal and first electronic data, and said first electronic data stored, at least temporality, by said computer program for comparison with second electronic data representing said second sensed pressure signal.

11. A method of determining proper tubing installation in a peristaltic pump of the type having a pumping mechanism capable of receiving a tubing, and comprising the steps of:
(a) receiving a tubing into said linear peristaltic pump;
(b) closing the tubing at a point downstream from the pumping mechanism;
(c) engaging the pump mechanism and partially moving the pump mechanism forward to build pressure in the tubing and then stopping movement;
(d) sensing a first pressure in the tubing between the pumping mechanism and the downstream point of closing;
(e) sensing a second pressure in the tubing between the pumping mechanism and the downstream point of closing at a predetermined time after stopping; and
(f) comparing the second pressure to the first pressure and activating an alarm if the second pressure is less than the first pressure by at least a predetermined amount.

12. A method of determining proper tubing installation in a peristaltic pump of the type having a pumping mechanism capable of receiving a tubing, and comprising the steps of:
(a) receiving a tubing into said linear peristaltic pump;
(b) closing the tubing at a point downstream from the pumping mechanism;
(c) sensing an initial pressure in the tubing;
(d) engaging the pump mechanism and partially moving the pump mechanism forward to build pressure in the tubing and then stopping movement;
(e) sensing a first pressure in the tubing between the pumping mechanism and the downstream point of closing immediately after stopping movement of the pumping mechanism;
(f) comparing the initial pressure to the first pressure and activating an alarm if the first sensed pressure is not at least a predetermined amount greater than the initial sensed pressure.

13. A method of determining proper tubing installation in a peristaltic pump as in claim 12 further comprising the steps of:

(a) sensing a second pressure in the tubing between the pumping mechanism and the downstream point of closing at a predetermined time after stopping; and
(b) comparing the second pressure to the first pressure and activating an alarm if the second pressure is less than the first pressure by at least a predetermined amount.

* * * * *